(12) United States Patent
Kwak

(10) Patent No.: US 6,841,136 B2
(45) Date of Patent: Jan. 11, 2005

(54) LIGHTING EQUIPMENT HAVING AN ANION GENERATOR

(75) Inventor: Kyung Bae Kwak, Seoul (KR)

(73) Assignee: Donovan Dongsoon Kwak, Edgewater, NJ (US)

( * ) Notice: Subject to any disclaimer, the term of this patent is extended or adjusted under 35 U.S.C. 154(b) by 413 days.

(21) Appl. No.: 10/049,234

(22) PCT Filed: Dec. 29, 2002

(86) PCT No.: PCT/KR01/02282

§ 371 (c)(1),
(2), (4) Date: Feb. 11, 2002

(87) PCT Pub. No.: WO03/042601

PCT Pub. Date: May 22, 2003

(65) Prior Publication Data

US 2004/0047772 A1 Mar. 11, 2004

(30) Foreign Application Priority Data

Nov. 15, 2001 (KR) .......................... 2001-71131

(51) Int. Cl.[7] .............................. B01J 19/08; B03C 3/00
(52) U.S. Cl. .................. 422/186.03; 422/186; 422/122; 422/123; 95/57; 96/15; 96/16; 96/98
(58) Field of Search ................................ 422/122, 123, 422/186, 186.03; 95/57; 96/15, 98, 16

(56) References Cited

U.S. PATENT DOCUMENTS 6,464,499 B1 * 10/2002 Lu .............................. 433/92
6,713,026 B2 * 3/2004 Taylor et al. .......... 422/186.04

* cited by examiner

*Primary Examiner*—Steven Versteeg
(74) *Attorney, Agent, or Firm*—Birch, Stewart, Kolasch & Birch, LLP

(57) ABSTRACT

A lighting equipment for purifying air, includes an anion generator generating anions to purify air; a housing including an electric power source supplying an electric power, an amplifier amplifying the electric power from the electric power source, and an emitting aperture member having a plurality of holes for exhausting the generated anions therethrough; and at least one illumination unit engaged with the housing.

16 Claims, 3 Drawing Sheets

LIGHTING EQUIPMENT HAVING AN ANION GENERATOR

RELATED APPLICATION

The present application claims the benefit of Korean Patent Application No. 10-2001-0071131 filed on Nov. 15, 2001, under 35 U.S.C. §119, which is herein fully incorporated by reference.

BACKGROUND OF THE INVENTION

1. Field of the Invention

The present invention relates to a lighting device having an anion and, more particularly, to a lighting equipment which is integrated as a single unit with a conventional illumination device such as a lamp, and which is capable of varying the degree of air purification depending on the amount of anion generated by the equipment.

2. Description of Related Art

An air purification device commonly used to purify the air in a house or an office is known to produce a healthy indoor environment by removing various viruses, bacteria, tobacco smoke, etc. which would otherwise give out unpleasant odors. The use of the air purification device makes the indoor environment very pleasant and helps adjust the human body's balance. Air purification is achieved by the action of anions generated by an anion generator incorporated within the purification device. Such a purification device, however, uses a separate fan for creating a convection of indoor airs, which necessitates accommodating related parts such as a driving motor in the device. This kind of device has a disadvantage because it occupies a large space due to its large volume.

Recent versions of air purification devices do not employ fans described above for the purpose of miniaturizing the device. These devices, however, experience problems in their purifying ability due to the limited convection of air. Furthermore, since these miniaturized purification devices cover limited areas, a large number of the purification devices need to be installed to cover large areas which can be costly. Moreover, such purification devices require individual installation and maintenance, and multiple outlets for supplying power to these devices, which increases costs associated with the installation and use of purification devices.

To overcome these problems, Korean Patent No. 1997-6047 discloses a compactly structured conventional lighting device 1 as shown in FIG. 1. As shown in FIG. 1, the device 1 is integrated with multiple lamps 2, an electric power source 5, and an anion generator 4. The lamps 2 are engaged with a housing 3 of the device 1 for providing illumination. The anion generator 3 generates anions for purifying the air. There are, however, drawbacks associated with the device 1. Because the device 1 is configured to generate a fixed amount of anions on a continuous basis, the device 1 consumes much power. Further, since the anions are generated using high voltages that generate much heat, overheating of the device 1 occurs and the continuous use of the lamps is deemed extremely unsafe. Since the anion generator 4 projects and the width of the anion generator 4 is limited, the scope and direction of the anion generation is limited, such that the device 1 cannot adequately purify the indoor air.

Hence, there has been a long felt need in the art for an improved lighting equipment which solves the aforementioned problems and other problems associated with conventional lighting equipment.

SUMMARY OF THE INVENTION

Accordingly, an object of the present invention is to provide a lighting equipment having an anion generator which can purify indoor air without using fans and which can function as an illumination device.

It is another object of the present invention to provide a lighting equipment having an anion generator which can be rapidly turned on even at low ambient temperatures.

It is still another object of the present invention to provide a lighting equipment having an anion generator which eliminates the necessity of using fans, and thus lends itself to a simple manufacture in a compact size.

It is still another object of the present invention to provide a lighting equipment having an anion generator which is configured to emit anions through emitting apertures for applying a wide scope and direction of anion generation so as to purify the indoor air, whereby the lighting equipment of the present invention is without limitations of conventional illumination devices.

Briefly described, the present invention is directed to a lighting equipment for purifying air, comprising an anion generator generating anions to purify air; a housing including an electric power source supplying an electric power, an amplifier amplifying the electric power from the electric power source, and an emitting aperture member having a plurality of holes for exhausting the generated anions therethrough; and at least one illumination unit engaged with the housing.

Furthermore, the present invention is directed to a method of providing air purification using a lighting equipment having a housing engaged with at least one illumination unit, the method comprising the steps of supplying power to the housing through an electric power source; amplifying the electric power and supplying the amplified power to an anion generator in the lighting equipment; generating anions by the anion generator; and exhausting, through an emitting aperture member of the housing, the generated anions to outside of the housing to purify air.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

A preferred embodiment of the present invention is directed to a lighting equipment having an anion generator capable of providing mainly two functions: illumination such as in a lamp and air purification. The lighting equipment of the present invention includes a housing and at east one lamp supported on the housing. The housing contains an anion generator member, an electron gun, an amplifier, an inverter, and an emitting aperture.

Figure 1:
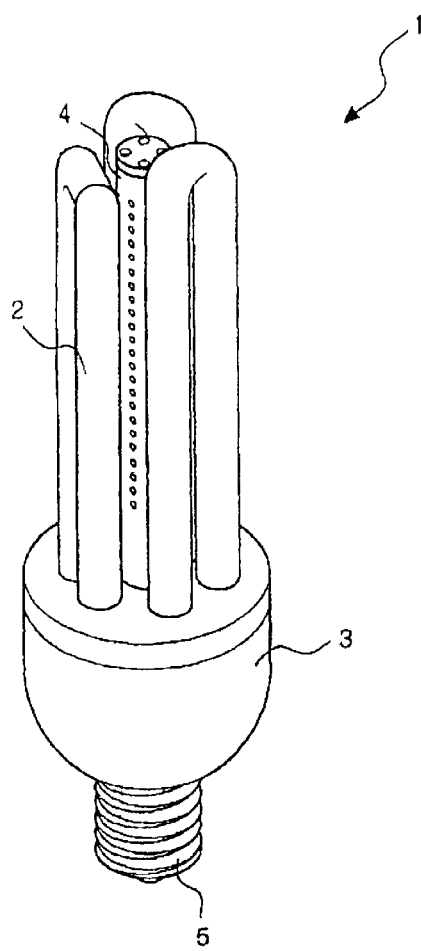
FIG. 1 is a perspective view of a conventional lighting equipment having an anion generator.
Figure 2:
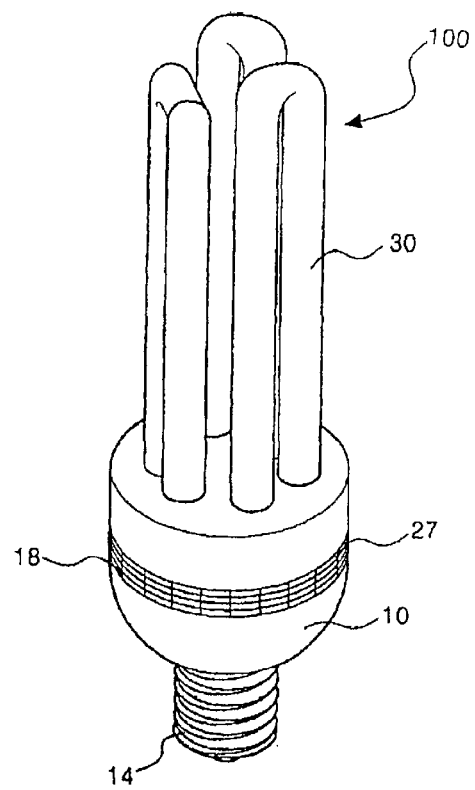
FIG. 2 is a perspective view of a lighting equipment having an anion generator according to a first embodiment of the present invention.
Figure 3:
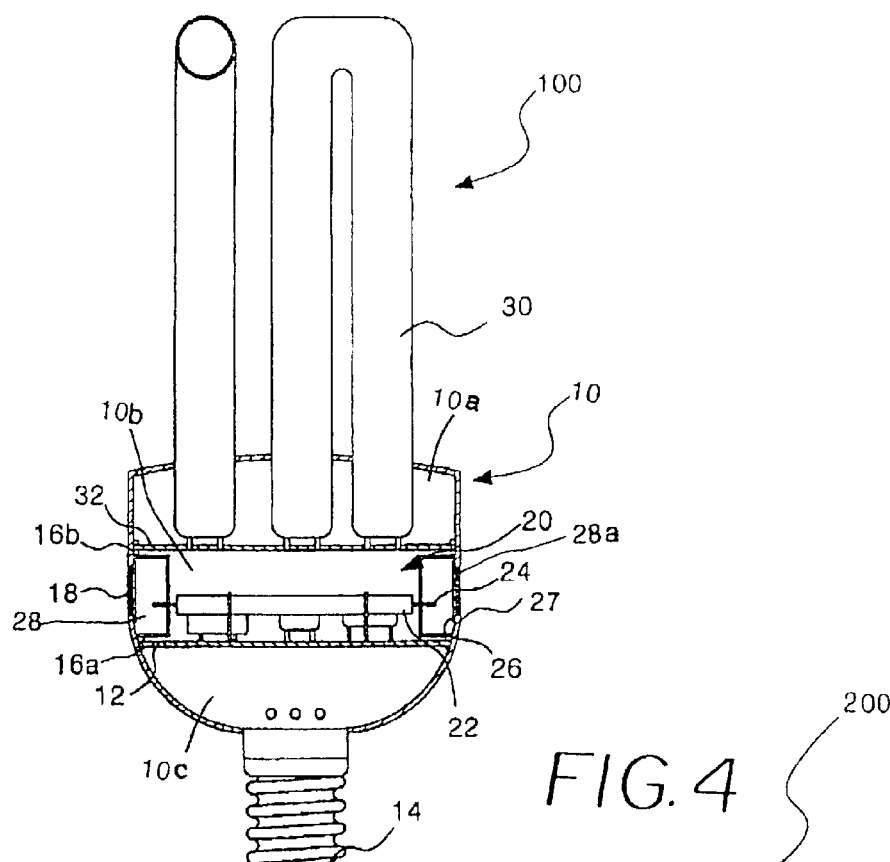
FIG. 3 is a partially cutaway exploded view of the anion generator of the lighting equipment of FIG. 2 according to the first embodiment of the present invention.

Referring now in detail to the drawings for the purpose of illustrating the preferred embodiment of the present invention, FIG. 2 is a perspective view of a lighting equipment 100 according to a first embodiment of the present invention. As shown in FIG. 2, the lighting equipment 100 includes a housing 10, at least one lamp or illumination unit 30 engaged with the housing 10, an electric power source 14 attached to the bottom of the housing 10, and an anion generator 20 disposed within the housing 10. The housing 10 has a tubular configuration (FIG. 3). All these components are operatively coupled.

FIG. 3 is a cross-sectional view of the lighting equipment 100 in FIG. 2. As shown in FIG. 3, the housing 10 is divided into upper, middle, and lower parts 10a, 10b, and 10c by lower and upper supporting member 16a and 16b, and includes an emitting aperture member 18 disposed at the walls of the middle part 10b (FIG. 2) and having a plurality of slits or openings 27 for emitting therethrough anions generated within the housing 10. In this example, the emitting aperture member 18 is disposed along the entire circumference of the housing 100; however, the emitting aperture member 18 can be in any shape, configuration, and/or size depending on the application. Further, the different parts 10a, 10b and 10c of the housing 10 can be individually produced and assembled together as one unit.

The electric power source 14 is spiraled shaped, e.g., in the shape of a screw, and is attached to the bottom of the lower part 10c of the housing 10. The electric power source 14 is assembled with a conventional power socket (not shown) to receive supply voltages from an external power source.

The lighting equipment 100 further includes an amplifier 12 or the like disposed on or supported, by the lower supporting member 16a, and an inverter 32 or the like disposed on or supported by the upper supporting member 16b. The amplifier 12 amplifies power or voltages received from the electric power source 14 into high voltages, and supplies or can supply power to any part in the lighting device 100 as needed. The amplifier 12 may include, but is not limited to, a transformer and/or other related electronic components and circuitry disposed on a printed circuit board. The inverter 32 supplies power to the lamps 30. The operation of the inverter 32 and the amplifier 12 is well known in the art.

The anion generator 20 is disposed within the middle hollow part 10b of the housing 10 under the lamps 30. The anion generator 30 includes an anion collecting panel 28 functioning as a cathode, an electron plate 26 one or more electron guns 24 functioning as an anode, and an anion generating plate 22. The outer circumferential surface of the anion collecting panel 28 includes a plurality of openings 28a that connect with the openings 27 of the housing 10. Such openings 28a and 27 may be arranged at regular intervals to form and inlet (or outlet) for the air. In one example, the openings 28a of the panel 28 and the openings 27 of the housing 10 take a circular shape and are disposed around the entire outer middle circumference area of the housing 10. Further, the electron guns 24 may be disposed at regular intervals around and near the middle inner circumference of the housing 10. As such, the electron plate 26 may be in a similar shape to be coupled with the electron guns 24. For instance, the electron plate 26 may have a ring shape and the electron guns 24 may be disposed in a ring configuration. However, the present invention is not limited to such, but includes other shapes, configurations, and/or sizes for the openings, electron guns, and/or the electron plate depending on the need or application.

The anion generator plate 22 receives the high voltage from the amplifier 12 and emits electrons to the plurality of electron guns 24. At this time, the electrons from the electron guns 24 crash against the electron plate 26 and then generate anions. The generated anions are collected in the anion collecting panel 28 and then discharged to the outside of the housing 10 through the openings 28a of the anion collecting panel 28 and the openings 27 of the housing 10.

Each electron gun 24 is installed at the center portion within the anion collecting panel 28, so that it is preferably spaced apart at a constant distance from the inner circumferential surface of the anion collecting panel 28. Each electron gun 24 can be made with a material such as copper, aluminum, brass, etc. Each electron gun 24 includes a plurality of discharge electrodes which are arranged at regular intervals and which extend in the longitudinal direction. The outer edges of the discharge electrodes may be sharply shaped. Each electron gun 24 is fixed to the electron plate 26.

The operation of the lighting equipment 100 is as follows according to one embodiment of the present invention. The electric power source 14 is assembled with a conventional power socket (not shown) and a power switch (not shown) disposed at the housing 10 is turned on, whereby power is supplied to the electric power source 14, the amplifier 12 and the inverter 32. The inverter 32 supplies power to the lamps 30 and the lamps 30 emit light therefrom. The amplifier 12 generates and supplies amplified voltages to the anion generator 20 to generate anions. Particularly, the anode voltage generated by the amplifier 12 is applied to both ends of the electron gun 24 while the cathode voltage generated by the amplifier 12 is applied to the anion collecting panel 28. Depending on the voltages supplied to the anion generator 20 by the amplifier 12, the amount of anions generated by the anion generator 20 can vary.

When the lamps 30 are turned on, a convection current is spontaneously formed around the anion generator 20 in the indoor air by the action of the heat emitted from the lamps 30. Accordingly, the air enters through the through the openings 27 and 28a. The air which enters these openings 27 and 28a is purified within the anion collecting panel 28 where anions generated from the discharge electrodes are collected. The purified air then exits to the outside through the openings 27 and 28a serving as outlets.

Figure 4:
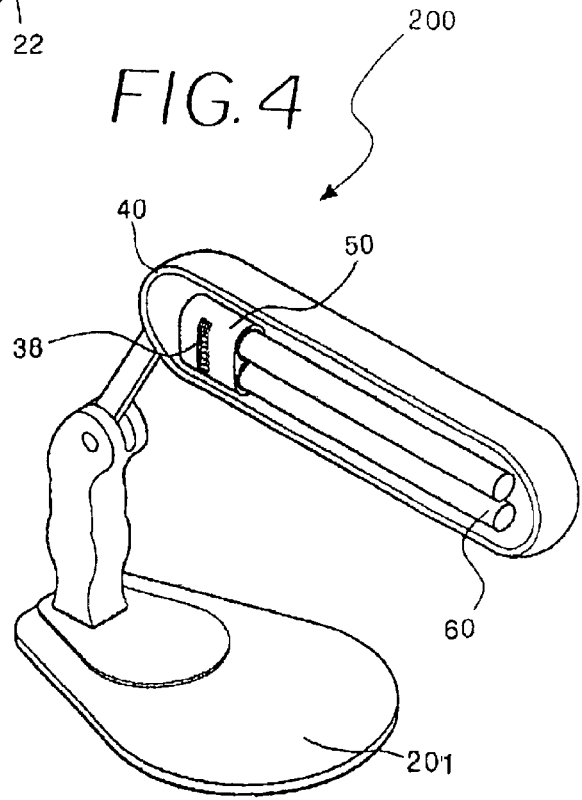
FIG. 4 is a perspective view of a lighting equipment having an anion generator according to a second embodiment of the present invention.
Figure 5:
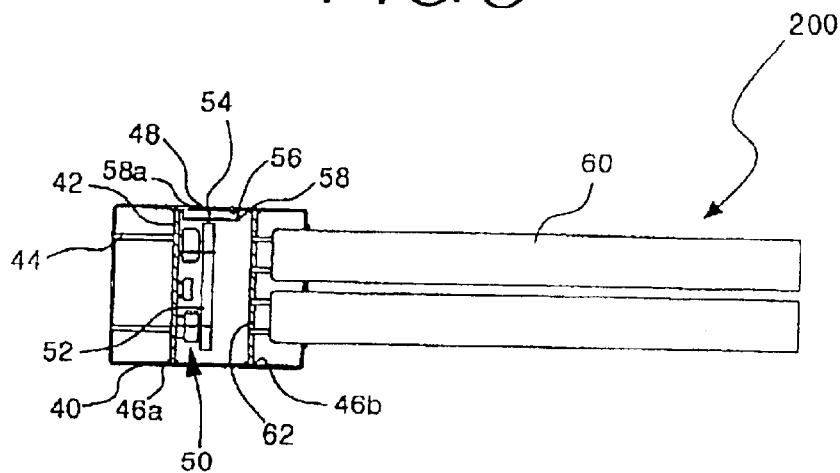
FIG. 5 is a partially cutaway exploded view of the anion generator of the lighting equipment of FIG. 4 according to the second embodiment of the present invention.

FIG. 4 is a perspective view of a lighting equipment 200 having an anion generator according to a second embodiment of the present invention, and FIG. 5 is a cross-sectional view of a portion of the lighting equipment 200 according to the second embodiment of the present invention. As shown in FIGS. 4 and 5, the lighting equipment 200 is identical or similar to the lighting equipment 100 of FIG. 2, except that lamps 60 are movably supported by a lamp stand 201, openings 38 of a housing 40 are disposed only one side of the housing 40 (requiring at least one electron gun 54 to be disposed only on one side of the housing 40). For instance, in the lighting equipment 200, the housing 40 contains an amplifier 42, an electric power source 44 providing power to the amplifier 42, an inverter 62, a pair of supporting members 46a and 46b fixedly supporting the amplifier 42 and the inverter 62 respectively, an emitting aperture member 48 having holes 38 for exhausting the generated anions to the outside thereof, and an anion generator 50 generating anions.

The anion generator 50 includes an anion generating plate 52, at least one electron gun 54 generating electrons, an electron plate 56 for crashing the electrons against to generate anions, and an anion collecting panel 58 for collecting the generated anions therein and having openings 58a directly connected with the openings 38 of the housing 40. The electron gun(s) 54 are preferably installed (at certain intervals) on one side of the housing 40.

Figure 6:
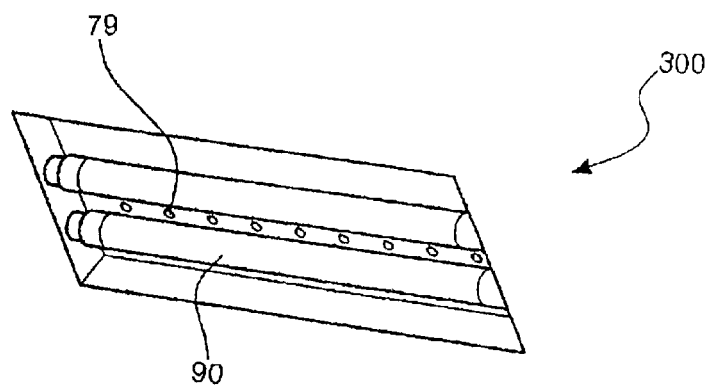
FIG. 6 is a perspective view of a lighting equipment having an anion generator according to a third embodiment of the present invention.
Figure 7:
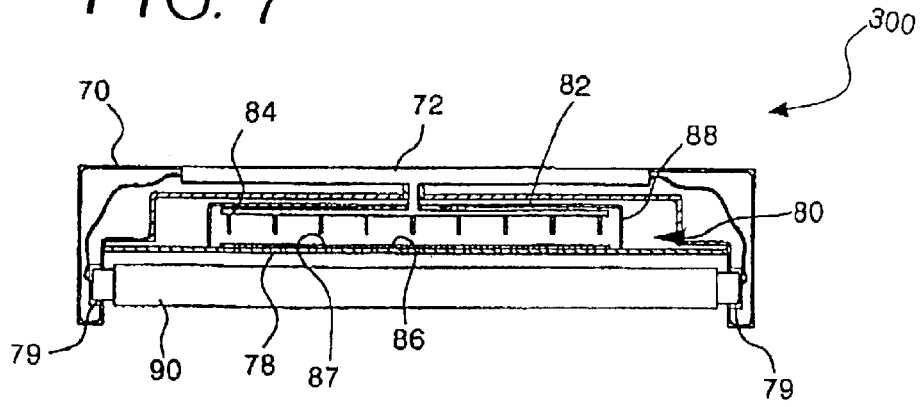
FIG. 7 is a partially cutaway exploded view of the anion generator of the lighting equipment of FIG. 6 according to the third embodiment of the present invention.

FIG. 6 is a perspective view of a lighting equipment 300 having an anion generator according to a third embodiment of the present invention, and FIG. 7 is a cross-sectional view of a housing of the lighting equipment 300 of FIG. 6 according to the third embodiment of the present invention. As shown in FIGS. 6 and 7, the lighting equipment 300 is identical or similar to the lighting equipment 100 of FIG. 2, except for the use of a fluorescent lamp 90 installed using known connecting means 79. Particularly, the lighting equipment 300 includes a housing 70 containing the lamp(s) 90 and an anion generator 80. The housing 70 further includes an amplifier 72 for amplifying voltages, and an emitting aperture member 78 having holes for emitting generated anions to the outside thereof. The anion generator 80 includes an anion generating plate 82 receiving high voltages from the amplifier 72 and generating electrons through a plurality of electron guns 84 being disposed at certain intervals, an electron plate 86 for crashing the electrons against to generate anions, and an anion collecting panel 88 collecting the generated anions and having openings 87 coupled with openings of the housing 79 to exhaust the generated anions to the outside of the housing to purify air. The electron guns 84 and the openings 87 are installed on one side of the housing 70.

The lamps in the present invention can be U-shaped tubes or any other types of tubes or lamps known in the art. If the lamps are used as fluorescent lamps, the lamps are equipped to provide conventional illumination functions. If the lamps are used as ultraviolet lamps, the lamps are equipped to generate ultraviolet rays which sterilize and eliminate various viruses.

Accordingly, the present invention provides a unique lighting equipment which provides effectively both light illumination and air purification and which promotes a safe and continuous use of the device.

The invention being thus described it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A lighting equipment for generating anions to purify air, the equipment comprising:

an anion generator generating anions to purify air;

a housing including,
   an electric power source supplying an electric power,
   an amplifier amplifying the electric power from the electric power source, and
   an emitting aperture member having a plurality of holes for exhausting the generated anions therethrough; and at least one illumination unit engaged with the housing.

2. The lighting equipment of claim 1, further comprising:

an inverter disposed in the housing for supplying electric power to the illumination unit.

3. The lighting equipment of claim 1, wherein the anion generator includes:

an anion generating plate receiving high voltages from the amplifier;

at least one electron gun coupled with the anion generating plate and generating electrons; and an electron plate interacting with the electron gun to generate anions from the electrons.

4. The lighting equipment of claim 3, wherein the anion generator further includes:

an anion collecting panel for collecting the generated anions therein and exhausting the anions therethrough and through the emitting aperture member.

5. The lighting equipment of claim 3, wherein the electron gun is only on one side of the housing.

6. The lighting equipment of claim 1, wherein the emitting aperture member is disposed only on one side of the housing.

7. The lighting equipment of claim 1, wherein the emitting aperture member is disposed around the entire circumference of the housing.

8. The lighting equipment of claim 1, wherein the illumination unit is a florescent lamp or a stand lamp.

9. A method of providing air purification using a lighting equipment having a housing engaged with at least one illumination unit, the method comprising the steps of:

supplying power to the housing through an electric power source;

amplifying the electric power and supplying the amplified power to an anion generator in the lighting equipment;

generating anions by the anion generator; and exhausting, through an emitting aperture member of the housing, the generated anions to outside of the housing to purify air.

10. The method of claim 9, further comprising:

illuminating the illumination unit by the electric power supplied by the electric power source.

11. The method of claim 9, wherein the generating step includes:

generating high voltages from the amplifying step;

generating electrons through at least one electron gun disposed in the housing; and causing the electrons to interact with an electron plate to generate anions.

12. The method of claim 11, further comprising:
   collecting, in an anion collecting panel disposed in the housing, the generated anions.

13. The method of claim 11, wherein the electron gun is only on one side of the housing.

14. The method of claim 9, wherein, in the exhausting step, the emitting aperture member is disposed only on one side of the housing.

15. The method of claim 9, wherein, in the exhausting step, the emitting aperture member is disposed around the entire circumference of the housing.

16. The method of claim 9, wherein the illumination unit is a florescent lamp or a stand lamp.

* * * * *